(12) United States Patent
Kligerman et al.

(10) Patent No.: US 6,692,254 B1
(45) Date of Patent: Feb. 17, 2004

(54) IMPLANT SUPPORTED DENTAL PROSTHESIS FOUNDATION BAR

(76) Inventors: Barry A. Kligerman, 9501 NW. 13th St., Plantation, FL (US) 33322; John C. Stone, 3101 N. Federal Hwy. Suite 501, Fort Lauderdale, FL (US) 33306; Michael Peterson, 300 NE. 4th St., Delray Beach, FL (US) 33444

( * ) Notice: Subject to any disclaimer, the term of this patent is extended or adjusted under 35 U.S.C. 154(b) by 41 days.

(21) Appl. No.: 10/061,649

(22) Filed: Feb. 1, 2002

(51) Int. Cl.$^7$ ................................................ A61C 8/00
(52) U.S. Cl. ...................................................... 433/173
(58) Field of Search ........................... 433/172, 173, 433/174, 194, 213

(56) References Cited

U.S. PATENT DOCUMENTS

| | | | |
|---|---|---|---|
| 3,748,739 A | * 7/1973 | Thebert | |
| 4,225,668 A | * 9/1980 | Bartoli | 433/176 |
| 4,529,384 A | * 7/1985 | Severy | 433/213 |
| 4,767,328 A | 8/1988 | Branemark | 433/168.1 |
| 4,906,191 A | 3/1990 | Soderberg | 433/213 |
| 4,986,753 A | 1/1991 | Sellers | 433/172 |
| 5,007,833 A | * 4/1991 | Barbone | 433/172 |
| 5,064,374 A | * 11/1991 | Lundgren | 433/173 |
| 5,219,286 A | * 6/1993 | Hader | 433/172 |
| 5,242,303 A | 9/1993 | De Buck | 433/213 |
| 5,286,196 A | * 2/1994 | Brajnovic et al. | 433/173 |
| 5,419,700 A | * 5/1995 | Sillard | 433/172 |
| 5,427,906 A | * 6/1995 | Hansen | 433/173 |
| 5,575,651 A | * 11/1996 | Weissman | 433/173 |
| 5,630,717 A | 5/1997 | Zuest | 433/172 |
| 5,752,828 A | 5/1998 | Andersson | 433/172 |
| 5,788,492 A | * 8/1998 | Weissman | 433/173 |
| 5,975,904 A | * 11/1999 | Spiegel | 433/176 |
| 6,056,547 A | 5/2000 | Names | 433/173 |

FOREIGN PATENT DOCUMENTS

EP 0 393 324 * 2/1990

OTHER PUBLICATIONS

Branemark, et al. "Branemark Novum" Clin. Implant Dent. Res. 1999:1: 2–16.

* cited by examiner

Primary Examiner—Ralph A. Lewis
(74) Attorney, Agent, or Firm—Alvin S. Blum

(57) ABSTRACT

Apparatus and method for fastening a denture plate with many artificial teeth to a plurality of implants screwed into the bone is disclosed that may be completed on the same day as surgical implantation of the implants. The denture plate is prepared before surgery. A rigid metal bar is prepared that is fitted to register with the implants after the implants have been implanted. The rigid metal bar is affixed to the denture plate. Screws through the bar are received into the top of each implant to thereby secure the bar and the attached denture plate to the implants. This distributes the tooth forces among the implants for enhanced function. The bar is composed of a metal attachment for each implant. A pair of wings extends out from each attachment. The attachments are temporarily mounted on the implants so that wings from adjacent attachments overlap. The attachments and wings are temporarily joined with cement. The cemented bar is mounted on a support, the cement removed, and the bar fastened together permanently. The bar is then attached to the denture and the combination mounted on the implants.

7 Claims, 4 Drawing Sheets

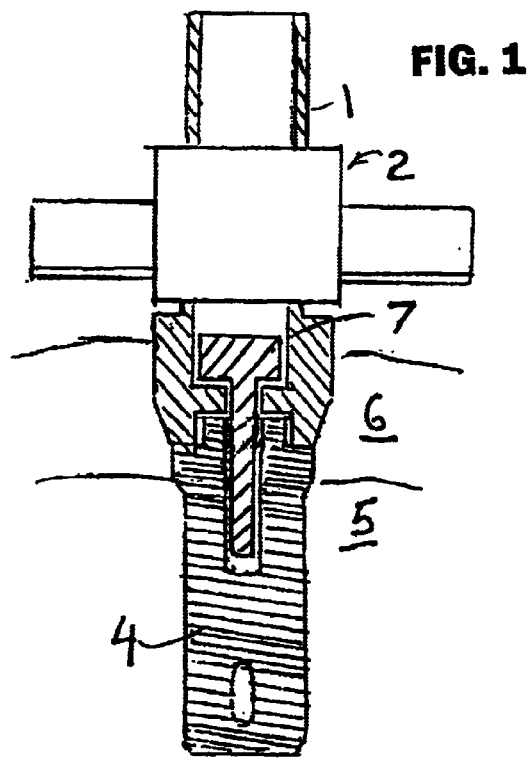
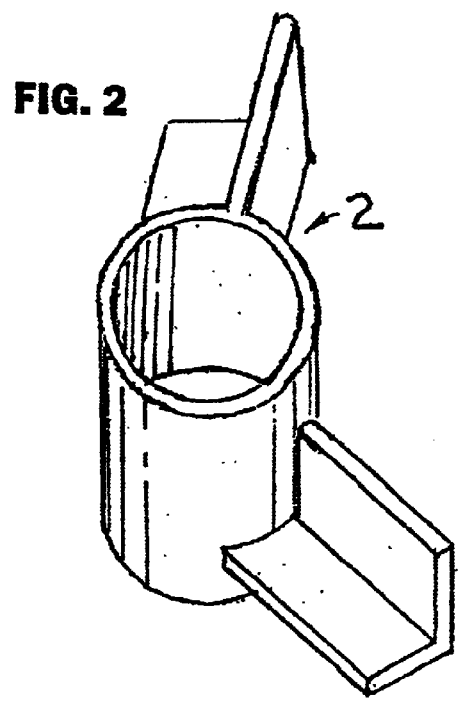
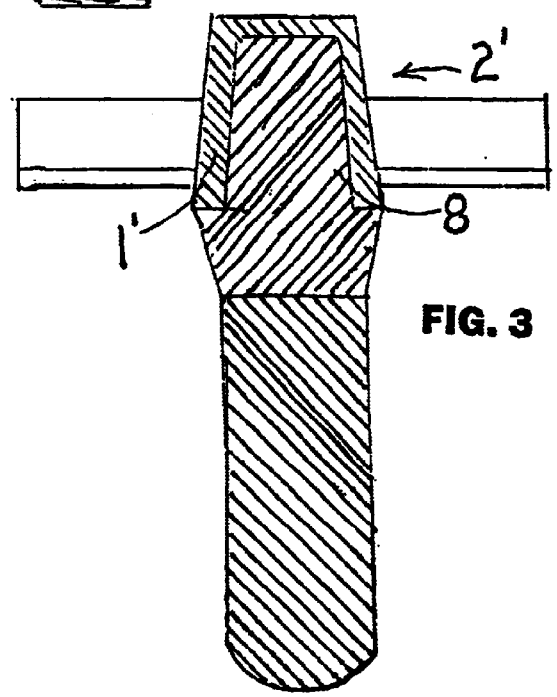
FIG. 1
FIG. 2
FIG. 3

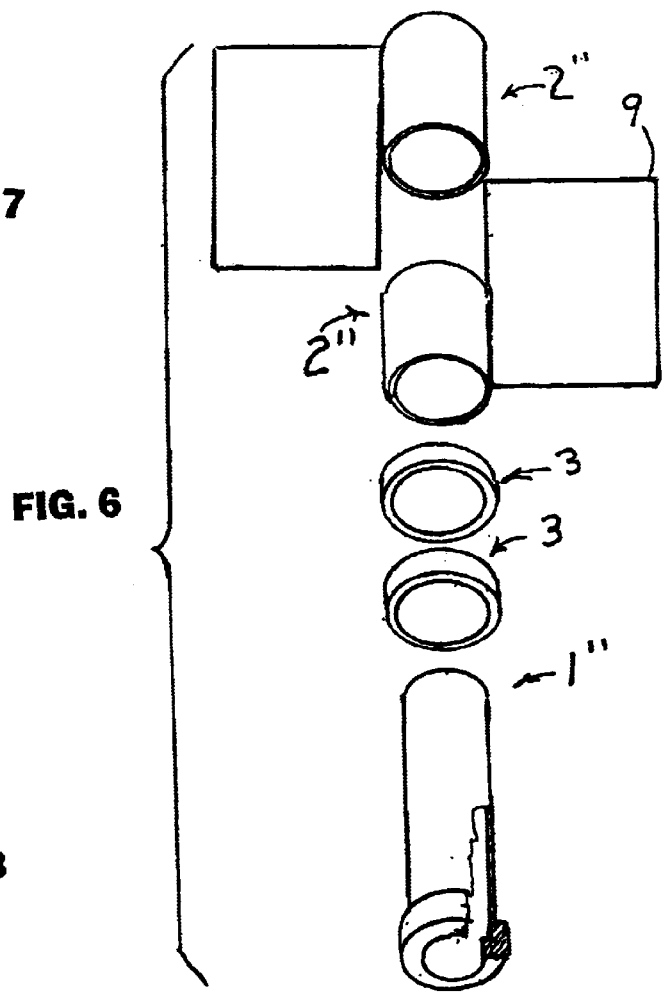
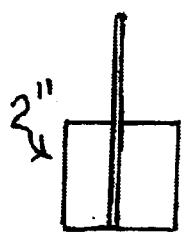
FIG. 7
FIG. 6
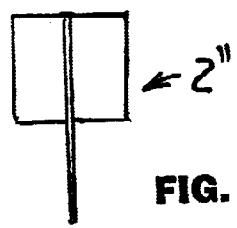
FIG. 8
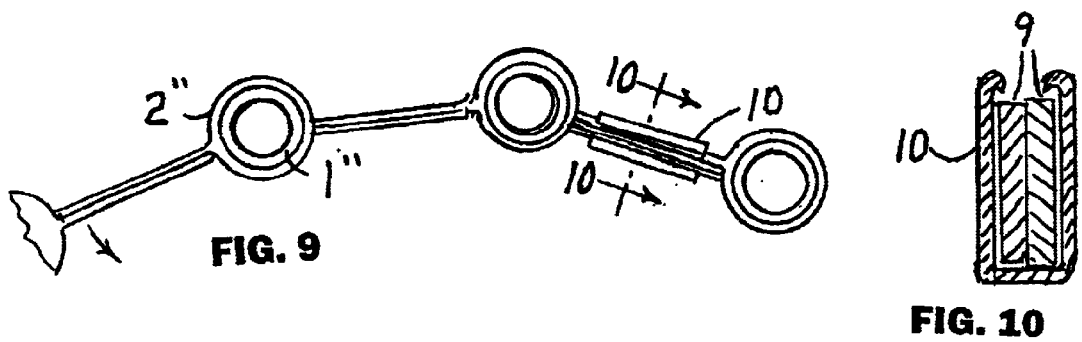
FIG. 9
FIG. 10

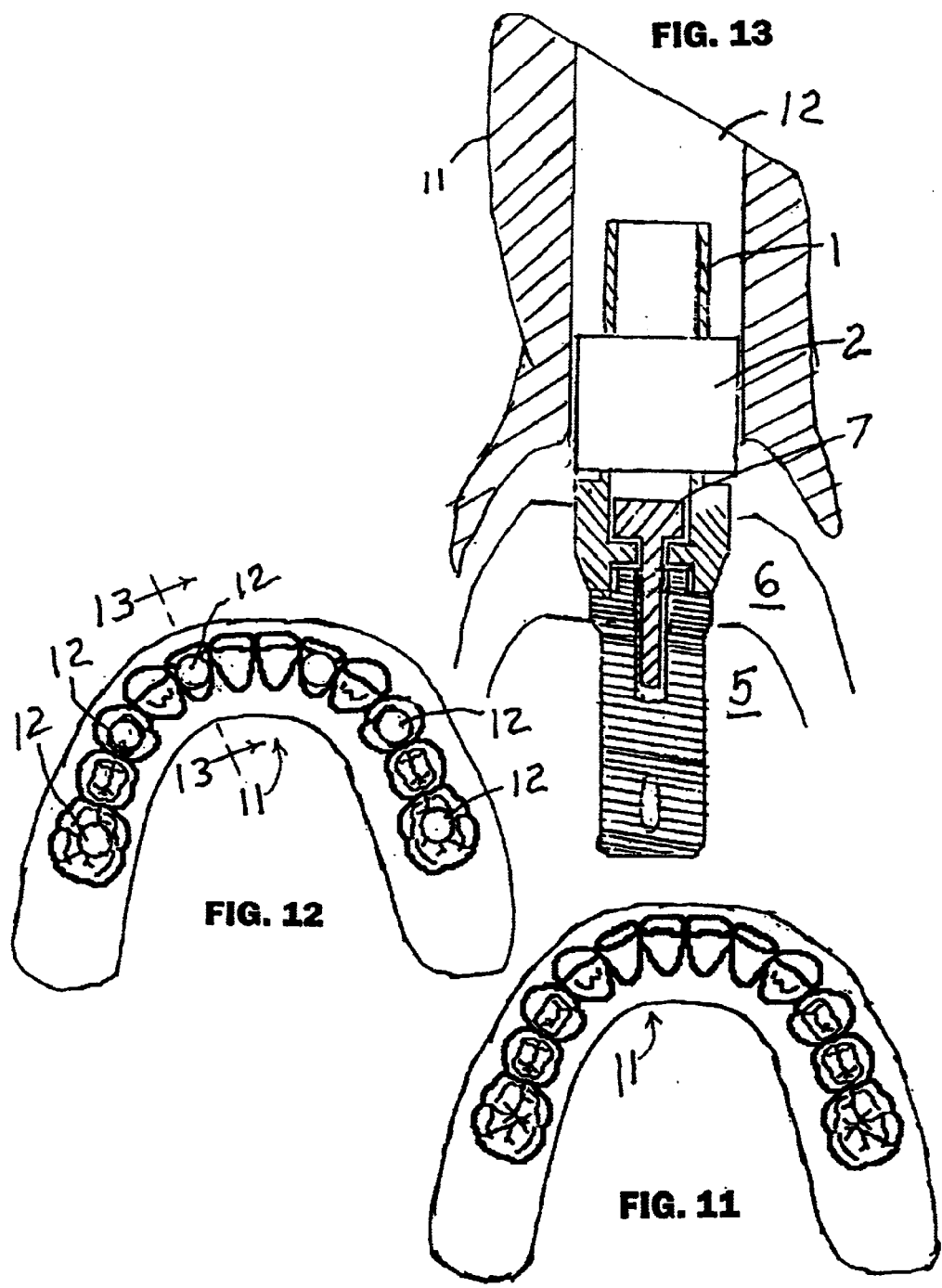

US 6,692,254 B1

IMPLANT SUPPORTED DENTAL PROSTHESIS FOUNDATION BAR

This invention relates to a plurality of artificial teeth supported by a plurality of implants, and more particularly to a means and method of preparing a rigid metal bar that is fitted to implants embedded in the bone. The bar, in turn, supports a dental prosthesis with many teeth, all installed on the same day as surgical installation of the implants.

BACKGROUND OF THE INVENTION

When a tooth is missing, it is often useful to surgically insert a metal implant screwed into the bone to support an artificial tooth. Recent developments in the art have made it possible to complete the surgical implantation and installation of the tooth on the same day. When many teeth are to be replaced, it is common to prepare a rigid metal bar or bridge to be fastened to a plurality of implants. A denture with many replacement teeth is then fastened to the metal bar. This makes it possible to support many teeth, with as few as three implants. It also enables the forces on the teeth to be distributed onto many implants at once for greater resistance to damage to the restoration. Branemark et al. describe a system of this sort that may be completed on the day of surgery. That method involves the use of a primary bar and a secondary bar with holes positioned for receipt of retaining screws. The soft tissue over the bone is moved away to expose the bone. The crest of the bone is then planed flat to correspond to the bottom of the primary bar. The bar is held in place on the bone to serve as a template or drill jig for drilling the holes for the implants at the holes in the bar. The bar is removed, the holes drilled into the bone, and the implants screwed into the bone. The implants are each fitted with a collar that passes through the soft tissue and the soft tissue closed over the bone and sutured in the usual manner. A dental plate, or denture, is attached to the secondary bar. After the implants have been inserted surgically, the primary bar is screwed onto the implants and the secondary bar with attached denture is screwed onto the primary bar.

It would be useful to avoid having to expose and plane the crest of the large bone area as required by this procedure. Practitioners of the art are expert at finding the most suitable area for insertion of each implant for best results. This procedure dictates the location of the implants. Many dentists would prefer to have a denture prepared in advance by a dental laboratory, and to be able to position the implants based on the patient's situation.

SUMMARY OF THE INVENTION

It is accordingly an object of the invention to provide a means and method of supporting a dental prosthesis with many artificial teeth on a lesser number of surgically inserted implants, in which the entire procedure of insertion of implants and supporting the prosthesis thereon can be achieved in one day without the necessity of planing the crest of the bone or dictating the location of the implants. It is another object that the prosthesis may be prepared prior to the day of surgery, so that it may be prepared by an outside laboratory. It is yet another object that the means include a rigid metal bar that is fitted to the implants and that will support the prosthesis. It is yet another object that the bar be composed of a plurality of prefabricated individual components each of which fits onto an implant and that has projecting elements. It is yet another object that the projecting elements be cementable together while mounted on the implants to fix the bar geometry. It is yet another object that the elements be securely affixed together by soldering, welding or other permanent metal joining means without altering the bar geometry so that the rigid metal bar can be custom made to fit the patient on the day of operation.

These and other objects, features, and advantages of the invention will become more apparent when the detailed description is studied in conjunction with the drawings in which like elements are designated by like reference characters in the various drawing figures.

BRIEF DESCRIPTION OF THE DRAWINGS

FIG. 1 is a partially sectional view of an implant in the jaw with a tube and wing assembly in place.

FIG. 2 is a perspective view of a wing assembly.

FIG. 3 is a partial sectional view of another embodiment of the invention with a cementable wing assembly.

FIG. 6 is a perspective exploded view of another embodiment of the invention with adjustable wing angles.

FIG. 7 is an end view of the lower wing assembly.

FIG. 8 is an end view of the upper wing assembly.

FIG. 9 is a top view of several tubes with wing assemblies thereon.

FIG. 10 is a sectional view taken on line 10—10 of FIG. 9.

FIG. 11 is a top view of a denture plate prior to the procedure.

FIG. 12 is a top view of the plate of FIG. 11 after grinding away holes for receipt of the tubular members and screws.

FIG. 13 is a sectional view taken through line 13—13 of FIG. 12 after completion of the restoration.

DETAILED DESCRIPTION OF PREFERRED EMBODIMENTS

Figure 5:
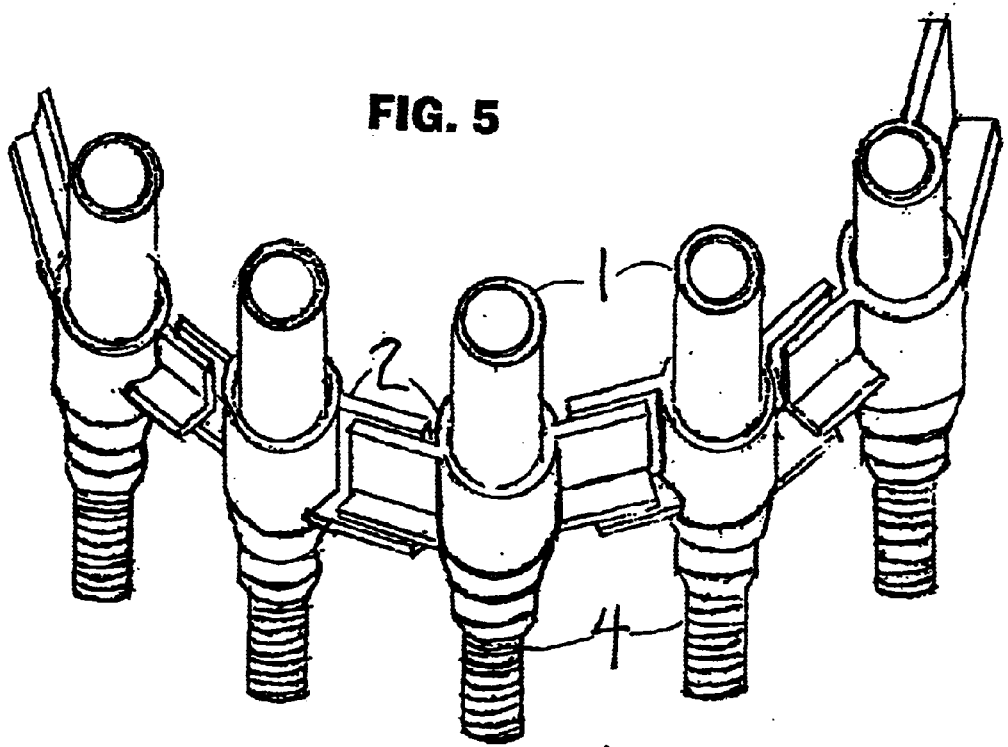
FIG. 5 is a perspective view as in FIG. 4 with wing assemblies on the tubular members prior to cementing.
Figure 4:
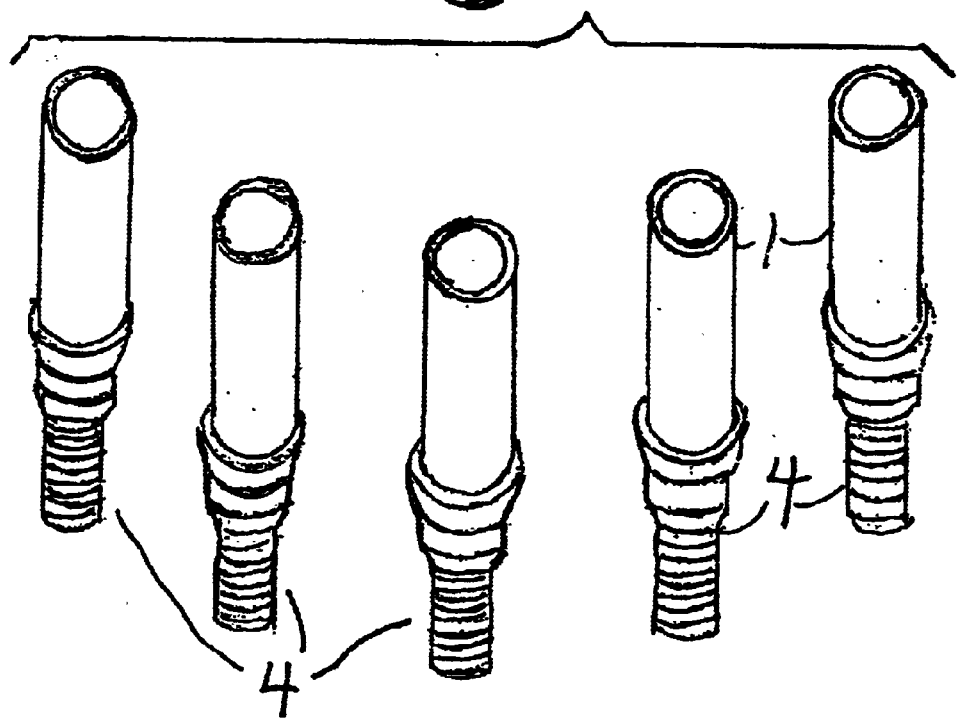
FIG. 4 is a perspective view of a plurality of implants in the bone with tubular members in place.

Referring now first to the drawing FIGS. 1,2,4, and 5, a first embodiment comprises a tubular member 1 and a wing assembly 2 fitting onto the member 1 that are mounted on the implant 4 that has been screwed into the bone 5 through the gum 6. A screw 7 removably attaches the tubular member 1 to the implant. A portion of the tubular member extends through the gum 6. The wings of adjacent wing assemblies overlap. Wing assemblies of various obtuse angles may be provided to enable selection of one most closely fitting the application. The components are temporarily bonded together with an adhesive such as acrylic to join all the tubes and wing assemblies together in one bar that fits exactly to the implants. The screws 7 are then removed so that the bar may be removed from the mouth. The cemented bar is then fitted to a mounting jig made of a heat resistant material(not shown) by means well known in the art. The cement is then removed from the cemented bar by heating. The jig maintains the position of all the components. The components are then rigidly fastened together, such as by soldering, bolts, welding, swaging, or the like. The resulting bar is a section of a polygon with straight lines formed by the wings between each screw receiving tubular element. The rigid, all-metal bar is then removed from the jig and fitted to the denture. This requires grinding away a hole 12 to fit each tubular member and receive the screws 7 from above, and a groove underneath to receive the wings. After securely mounting the bar with securely attached plate to the implants, the holes for the screws and any remaining spaces are filled in with restoration material to present a finished appearance and function. This is best seen in FIGS. 11–13.

In the alternative embodiment shown in FIG. 3, the abutment passing through the gum terminates in a tapered projection 8. The wing assembly 2' for this application includes a tapered tube 1' that is cemented to the projection without the use of a screw. The invention can also be employed with other types of implants well known in the art, such those having an abutment fixed to the implant, and those in which the abutment is a separate component that is fastened atop the implant. Abutment is a term applied to an extension above the implanted portion that extends through the gum.

The method of the invention with separate tubular members and wing assemblies comprises the following steps:
1. Prior to surgery, prepare dental plate prosthesis.
2. Insert implants surgically.
3. Mount each tube of device on each implant with screw.
4. Slide a wing assembly onto each tube.
5. Cement wings and tubes together to form a rigid cemented bar.
6. Unscrew cemented bar from implants.
7. Prepare heat resistant support and mount cemented bar on support.
8. Fire to drive off the cement.
9. Solder wings and tubes together, or join by other fastening means.
10. Remove soldered bar from support.
11. Check bar on implants.
12. Cut away denture to receive bar.
13. Affix bar to prosthesis.
14. Screw bar with prosthesis onto implants.
15. Cover screws and bar with denture material.
16. Send patient home with new teeth in place.

Referring now to FIGS. 6–10, another embodiment of the invention is shown, in which the angle between the wings is adjustable to correspond exactly to the implant positions. Each tube member 1" receives two wing elements 2". These may be identical, with one inverted. A plurality of washers 3 may be slipped onto the tubular member 1" to adjust for different gum thickness, so the wing assembly is above the surface of the gum when the member 1" extends through the gum. When an abutment extends through the gum, the washers will not be necessary. Ends of the wings 9 may be trimmed away as required when the implants are close together. An alternative method of permanently fastening together overlapping wings 9 from adjacent tubular members is shown in the form of an elongate U-shaped channel 10 that snaps in place. This presents a smooth bottom surface adjacent the gum surface.

In yet another embodiment of the invention, the attachment means may be permanently joined together into a rigid bar while removably attached to the implants such as by adhesive means. The permanently fastened together bar may then be removed from the implants, and affixed to the denture. The combination is then attached to the implants, and any finishing of the restoration that may be required is performed.

The attachment means may be made, in whole or in part, of strong material other than metal.

While we have shown and described the preferred embodiments of our invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. A method for securing a plurality of artificial teeth in a dental plate to a plurality of implants fixed in bone below the gum, the method comprising:
   a) prior to surgery, preparing a dental plate prosthesis;
   b) inserting implants surgically in the bone;
   c) mounting a tubular member on each implant with a screw;
   d) sliding a wing assembly onto each tubular member;
   e) cementing wings of overlapping wing assemblies and tubes together;
   f) unscrewing the cemented bar from the implants;
   g) preparing a heat resistant support and mounting the cemented bar on the support;
   h) firing to drive the cement off the bar;
   i) fastening wing assemblies and tubular members rigidly together by metal fastening means;
   j) removing the fastened bar from the support;
   k) cutting away the denture plate prosthesis to receive the bar;
   l) affixing the fastened bar to the prosthesis;
   m) screwing the bar with prosthesis attached onto the implants; and
   n) covering the screws and the bar with denture material.

2. A kit for securing a plurality of artificial teeth joined together in a tooth assembly to implants that are attached to the alveolar bone beneath gum in a mouth, the apparatus comprising:
   a) a plurality of metal attachment means for removably rigidly connecting to each implant;
   b) wing members extending laterally from the attachment means sufficiently to overlap wing members extending from adjacent attachment means;
   c) means for cementing the overlapping wing members together with cement while the attachment means are removably connected to the implants in the mouth to form a rigid bar in registry with the implants that may be removed from the mouth without disturbing that registry;
   d) means for removing the cement while holding the cemented bar in fixed position outside of the mouth;
   e) means for fastening the wing members together with fastening means while in that fixed position to form a permanent rigid metal bar in registry with the implants;
   f) means for affixing the permanent rigid metal bar to the tooth assembly while outside the mouth; and g) means for removably connecting the tooth assembly together with the rigid metal bar to the implants in the mouth.

3. The kit according to claim 2, in which the metal attachment means comprises a tubular member removably connectable to the implant and a sleeve that fits slidably on the tubular element, with two wing members being affixed to the sleeve.

4. The kit according to claim 2, in which a pair of wing members extend from the attachment means at an obtuse angle to one another.

5. The kit according to claim 2, in which the fastening means includes a generally U-shaped channel that snaps onto overlapping wing members.

6. The kit according to claim 2, in which the metal attachment means comprises a tubular member removably connectable to the implant and a pair of sleeves that fits slidably on the tubular element, one wing member being affixed to each of the pair of sleeves so as to provide an adjustable angle between the two wing members extending from the tubular member.

7. Apparatus for securing a plurality of artificial teeth joined together in a tooth assembly to implants that are attached to the alveolar bone beneath gum in a mouth, the apparatus comprising:

a) a plurality of attachment means for removably rigidly connecting to each implant;

b) wing members extending laterally from the attachment means sufficiently to overlap wing members extending from adjacent attachment means;

c) means for joining the overlapping wing members together while the attachment means are removably connected to the implants in the mouth to form a rigid bar in registry with the implants;

d) means for affixing the rigid bar to the tooth assembly outside the mouth; and e) means for removably connecting the tooth assembly together with the rigid bar to the implants in the mouth.

* * * * *